(12) United States Patent
Chen et al.

(10) Patent No.: US 7,358,078 B2
(45) Date of Patent: Apr. 15, 2008

(54) AUTO MICROFLUIDIC HYBRIDIZATION CHIP PLATFORM

(75) Inventors: Chien-An Chen, Hsinchu (TW); Meng-Yu Chen, Tou Fen (TW); Ming-Yuan Huang, Taipei Hsien (TW)

(73) Assignee: Dr. Chip Biotechnology Incorporation, Miaoli (TW)

(*) Notice: Subject to any disclaimer, the term of this patent is extended or adjusted under 35 U.S.C. 154(b) by 715 days.

(21) Appl. No.: 10/638,531

(22) Filed: Aug. 12, 2003

(65) Prior Publication Data
US 2004/0219661 A1   Nov. 4, 2004

(30) Foreign Application Priority Data
May 2, 2003   (TW) ................. 92112137 A

(51) Int. Cl.
*C12M 1/34*   (2006.01)

(52) U.S. Cl. ................. 435/286.5; 435/287.2; 435/288.5; 435/288.7; 435/293.1

(58) Field of Classification Search ............ 435/288.5, 435/293.1
See application file for complete search history.

(56) References Cited

U.S. PATENT DOCUMENTS

| | | | |
|---|---|---|---|
| 6,184,029 B1 * | 2/2001 | Wilding et al. ........... | 435/287.1 |
| 6,238,910 B1 | 5/2001 | Custance et al. | |
| 6,391,623 B1 * | 5/2002 | Besemer et al. ......... | 435/287.2 |
| 6,977,145 B2 * | 12/2005 | Fouillet et al. ............ | 435/6 |
| 2006/0160205 A1 * | 7/2006 | Blackburn et al. ....... | 435/287.2 |

* cited by examiner

*Primary Examiner*—William H. Beisner
(74) *Attorney, Agent, or Firm*—Rabin & Berdo, P.C.

(57) ABSTRACT

An auto microfluidic hybridization chip platform is disclosed to provide a hybrid reaction test system with the features of fast reactions, automatic operations, and a convenient platform. The platform includes a flow control system with a platform base, a microfluidic hybridization chip, a microfluidic hybridization chip support, a test agent support of the microfluidic hybridization chip; and a signal detection system. Using a microfluidic pipeline to connect various parts does not only realize automation and a small volume, but also increases the reaction speed.

20 Claims, 10 Drawing Sheets

AUTO MICROFLUIDIC HYBRIDIZATION CHIP PLATFORM

BACKGROUND OF THE INVENTION

1. Field of Invention

The invention relates to an auto microfluidic hybridization chip platform used for nucleic-acid hybridization reaction tests of samples.

2. Related Art

In recent years, molecular biology has made tremendous progress in its technology. For example, techniques such as PCR and nucleic-acid hybridization have been integrated with material sciences, bio-informatics, and electronic technology. This creates the new scope of biochips. In particular, the nucleic-acid hybridization reaction is a necessary and key procedure in the test procedures of molecular biology. The conventional nucleic acid hybridization procedure is complicated and time-consuming, which makes it the bottleneck step of the whole test. In general, hybridization reactions take about 4 to 12 hours. If one can simplify the operation and reaction time, the test can be introduced to usual point-of-care or home-care purposes. It will be the optimized solution for people being tested.

With complicated and time-consuming operation procedures, the conventional hybridization reactions require the uses of a hybridization box, a rotator, a vortex vibrator, and a scanning identification machine that cost a lot of money. Although there are already many international manufacturers in Europe, America, and Japan that apply automation technology to hybridization platforms requiring less manpower in place of the hybridization box, their specification still uses slides and cannot achieve the goal of mass filtering. For example, the products of Biogem, Genomic, PerkinElmer lifesciences, and Tecan all use such designs. The design disclosed in the U.S. Pat. No. 6,238,910 has the advantage that the hybridization chamber can accommodate two different sizes of slides. However, its drawback is also that the pipeline is exposed to the environment, inconvenient in operations.

The hybrid reaction platforms currently available on the market are designed according to the glass specification. The products are mainly for molecular biology laboratories, drug research and development institutes, and medical test centers. Most of them use high-density micro array probes. Moreover, due to their higher costs, such products are not popular in disease detection.

SUMMARY OF THE INVENTION

In view of the foregoing, the invention provides an auto microfluidic hybridization chip platform. It is designed to use a microfluidic chip within which all hybridization processes are completed. The size of the chip is about that of normal slides. The advantages of the micro fluid chip are its convenience and disposability.

The disclosed auto microfluidic hybridization chip platform includes a test agent support, a fluid control system and a microfluidic hybridization chip. The test agent support holds at least one test agent bottle containing a test agent. The test agent bottle is connected to the fluid control system and then to the microfluidic hybridization chip via a thin pipe and a connector. The fluid control system has at least a micro tunnel powered by air to control whether the test agent should flow through the micro tunnel to the microfluidic hybridization chip.

The microfluidic hybridization chip contains a sample receiving region, a mixing and denature region, and a hybridization and test region. The sample receiving region directly receives external samples. The fluid control system pushes the necessary test agents and samples to the mixing and denature region. Through the meander path of the mixing and denature region, the samples and test agents are fully mixed and denatured. Afterwards, the mixture enters the hybridization and test region.

Using such a platform, the devices required in the prior art (such as hybridization box, rotator, vortex vibrator, and scanning identification machine) are avoided. The operation procedure is simplified and the reaction time is reduced. Therefore, the invention can be popularized to point-of-care or home-care purposes.

BRIEF DESCRIPTION OF THE DRAWINGS

The invention will become more fully understood from the detailed description given hereinbelow illustration only, and thus are not limitative of the present invention, and wherein.

DETAILED DESCRIPTION OF THE INVENTION

Figure 1:
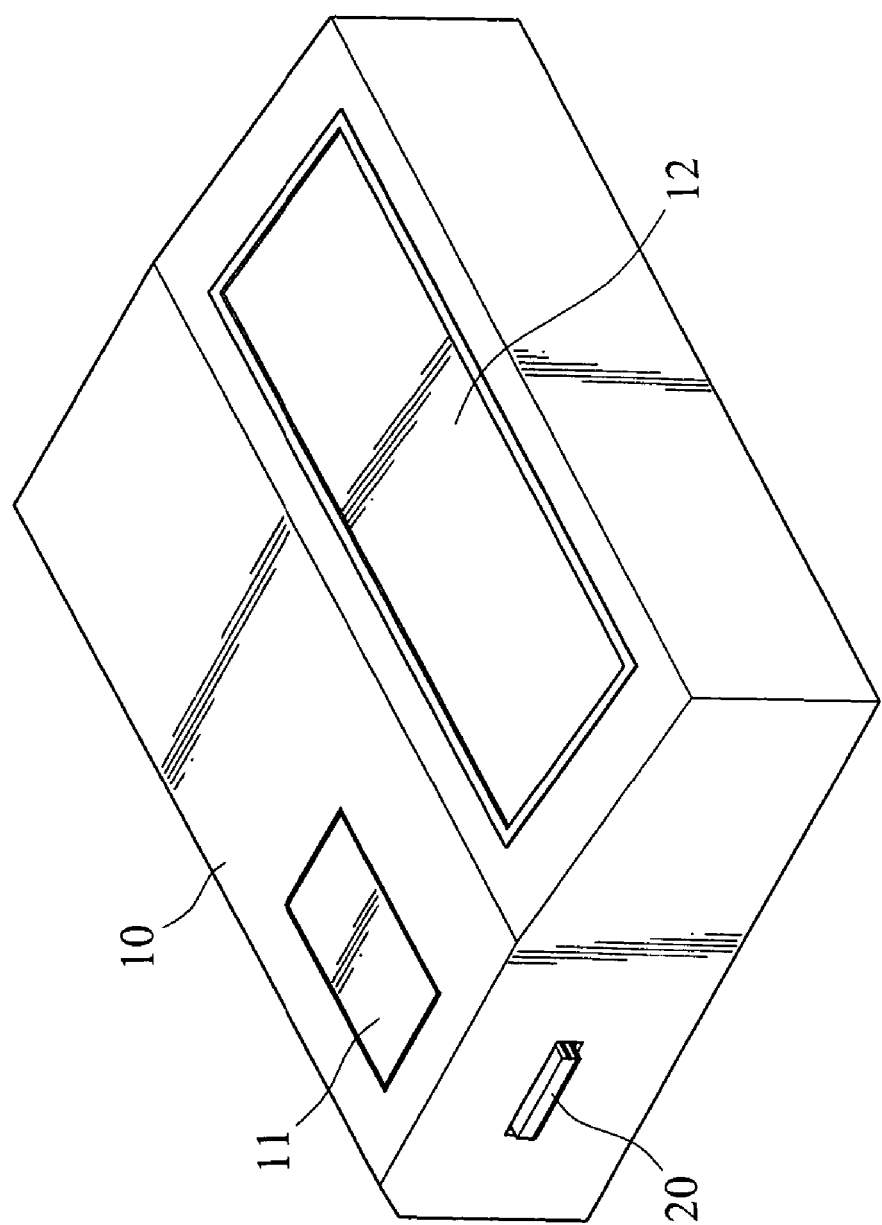
FIG. 1 is a schematic view of the appearance of the invention.
Figure 2:
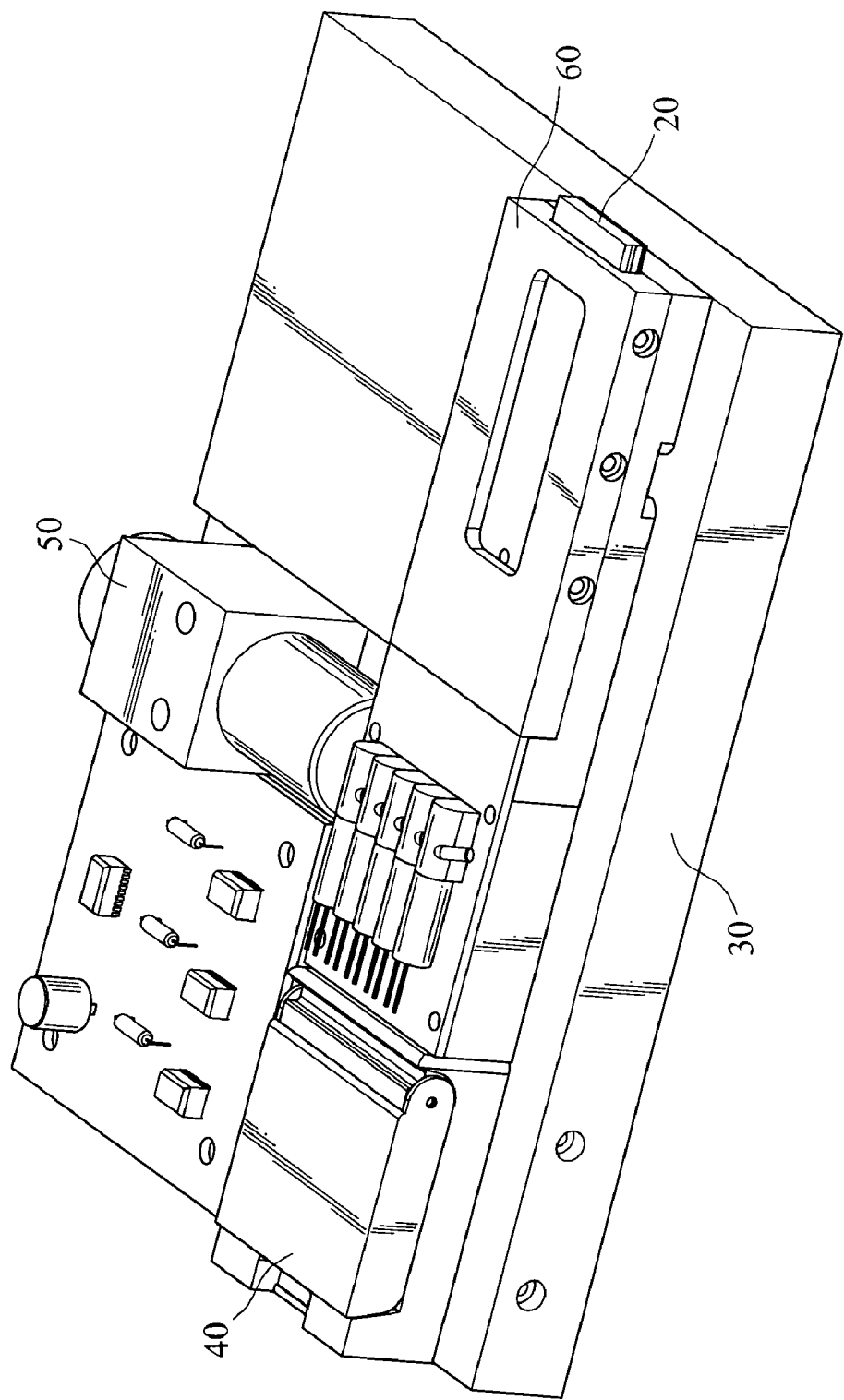
FIG. 2 is a schematic view of the invention.

With reference to FIG. 1, the disclosed auto microfluidic hybridization platform is covered by a case 100. One side of the case 10 is designed for the insertion of a microfluidic hybridization chip 20. That is, the invention is designed to be modularized according to different sample requirements. The top has a viewing window 11 formed from a transparent material and a control panel 12. One can check the reaction process and result via the viewing window 11 and put all control interfaces in the control panel 12. The internal structure is shown in FIG. 2. It includes a platform base 30, a microfluidic hybridization chip 20, a microfluidic hybridization chip support 60, a flow control system 50 of the microfluidic hybridization chip, a test agent support 40 of the microfluidic hybridization chip, and a signal detection system (see FIG. 11). The platform base 30 provides the functions of support. We describe the functions and structure of the rest parts in the following paragraphs.

Figure 3:
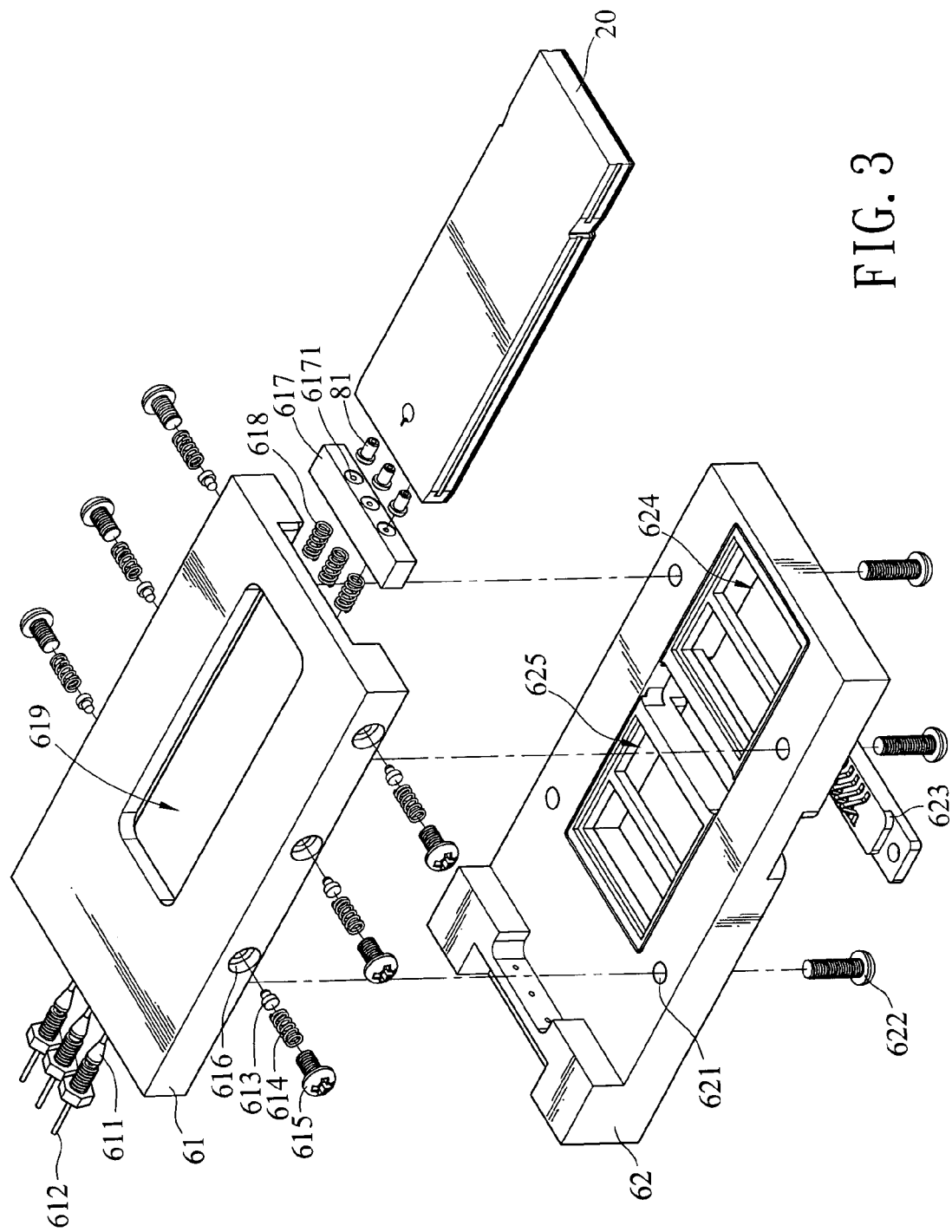
FIG. 3 is an exploded view of the disclosed microfluidic hybridization chip support.
Figure 4:
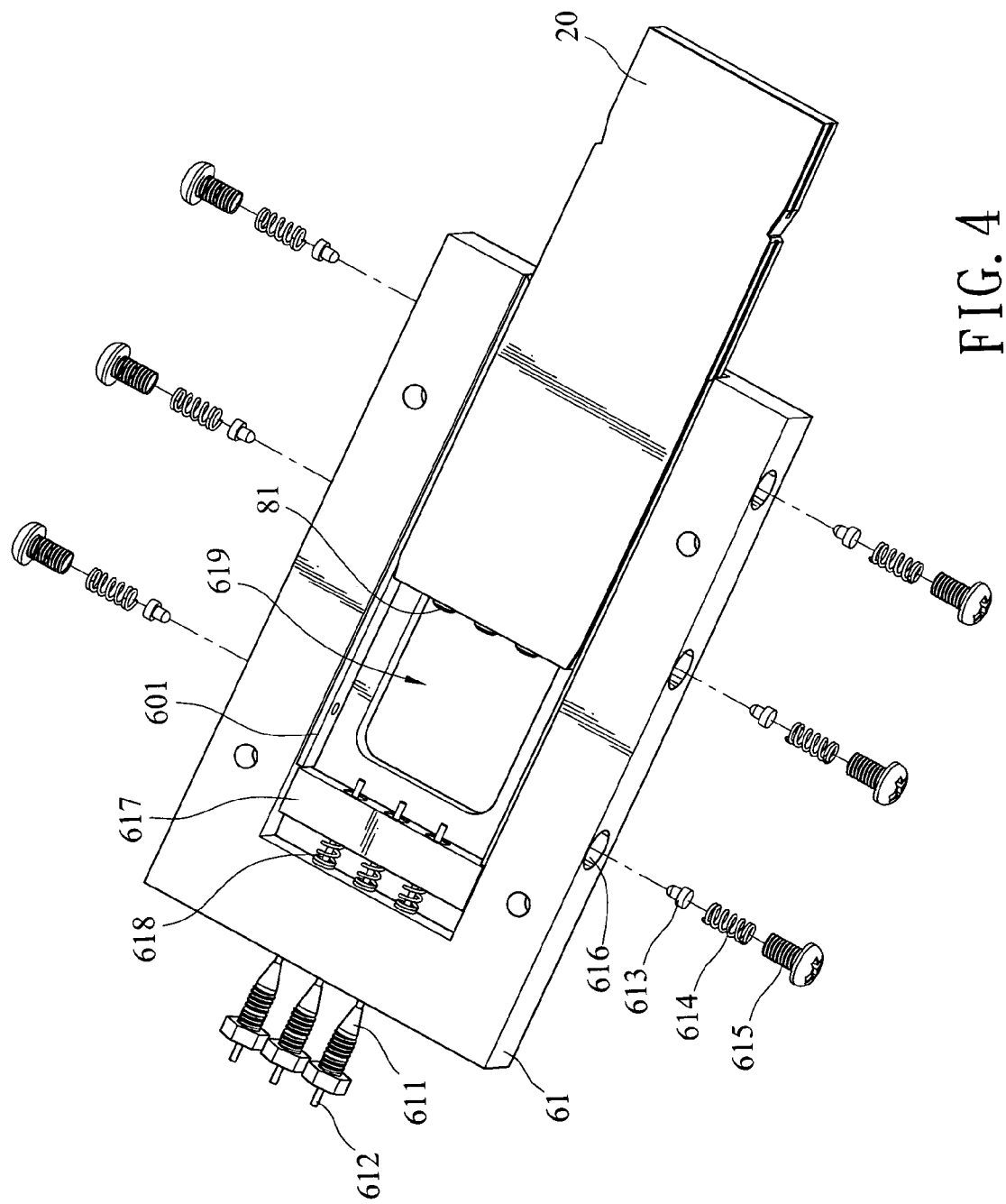
FIG. 4 is a schematic view of the microfluidic hybridization chip combined with the microfluidic hybridization chip support.

As shown in FIG. 3, the microfluidic hybridization chip support 60 is comprised of an upper cover 61 and a lower cover 62. It is used to support the microfluidic hybridization chip 20, which is fixed by several screws 622 penetrating through holes 621. On the other hand, the lower cover 62 has concaves 624, 625 for accommodating heating plates. These heat areas are designed for the microfluidic hybridization chip and will be explained in detail later. As shown in FIG. 4, the function of the upper cover 61 is to put the microfluidic hybridization chip 20 at a fixed position. The thin pipes 612 are the tunnels for the test agent to enter the microfluidic hybridization chip 20. The thin pipes 612 are fixed onto the upper cover 61 of the support module using ferrules 611 and screws. When the screws are driven in, the ferrules 611 tightly press the thin pipes 612. After the insertion of the microfluidic hybridization chip 20, it is fixed using positioning pins 613 along with the positioning holes 211 and the sliding track 212 on the chip. The front end of the microfluidic hybridization chip 20 has a slant angle for the user to insert the microfluidic hybridization chip support 60. Each positioning pin 613 goes through the corresponding hole 616 on the upper cover 61, with a spring 614 installed behind for pushing the positioning pin 613 outward. Its back is fixed using a screw 615. There are several positioning pins 613 in the drawing. They all have exactly the same structure and function. When the microfluidic hybridization chip 20 is inserted into the accommodation space 619 of the microfluidic hybridization chip support 60, the positioning pins 613 on both sides of the upper cover 61 push against the sliding tracks 212 of the microfluidic hybridization chip 20 (see FIG. 6) so that the microfluidic hybridization chip 20 does not move vertically. One can conveniently push the microfluidic hybridization chip 20 to the end. The bottom of the microfluidic hybridization chip support 60 has a sliding block combined with several springs 618. The sliding block 617 has corresponding holes 6171 for the thin pipes 612 to plug in. When the microfluidic hybridization chip 20 is pushed to the end, it depresses the springs 618 behind the sliding block 617 (FIG. 4). When the pushing force is removed, the microfluidic hybridization chip 20 is moved outward under the spring force of the springs 618. The positioning holes 211 on the microfluidic hybridization chip 20 arethen shifted to one of the positioning pins 613. Due to the spring force of the springs 614, the positioning pins 613 are pushed outward, inserting into the positioning holes 211 of the microfluidic hybridization chip 20. The microfluidic hybridization chip 20 is thus fixed here. After the test, one only needs to pull the microfluidic hybridization chip 20 out lightly to dismount the micro fluid hybridization chip 20. This kind of positioning means does not require complicated structural designs but achieves a high precision.

Figure 5:
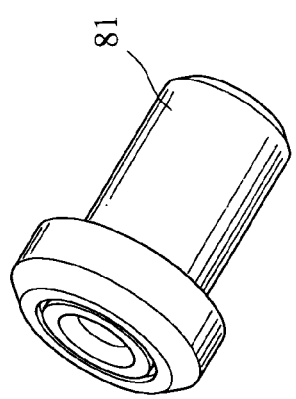
FIG. 5 is a schematic view of the elastic sleeve ring.
Figure 7:
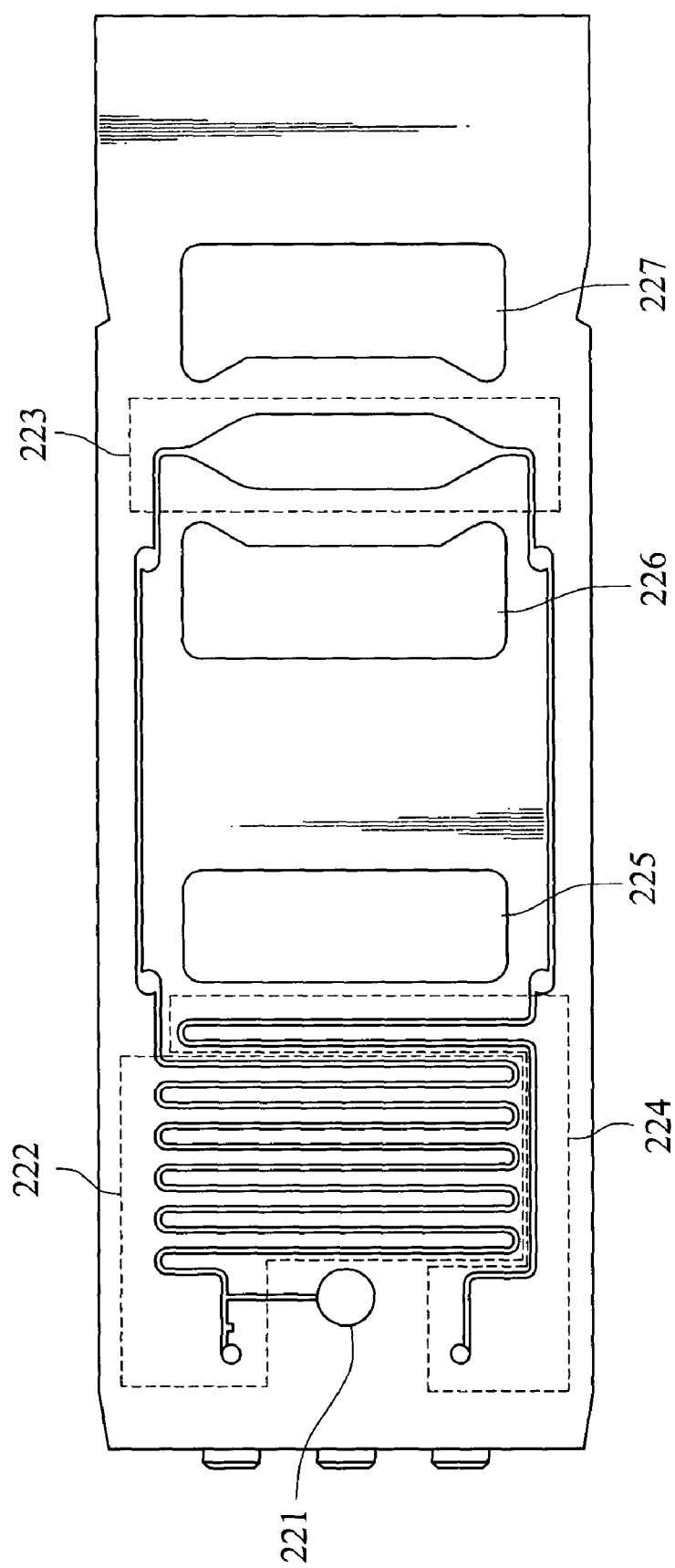
FIG. 7 is a top view of the microfluidic hybridization chip.

The connection between the tunnel inlet/outlet at the front end of the microfluidic hybridization chip 20 and the thin pipe 612 is sealed using an elastic sleeve ring 81. As shown in FIG. 5, after the microfluidic hybridization chip 20 is inserted into the microfluidic hybridization chip support 60, it depresses the springs 618 behind the sliding block 617. Once the pushing force is removed, the microfluidic hybridization chip 20 moves outward under the force of the springs 618. The micro fluid hybridization chip 20 is then fixed here. Depressing the springs 618 can push the sliding block 617, pressing the sliding block 617 tightly against the microfluidic hybridization chip 20. The elastic sleeve ring 81 is also depressed so that the connection between the tunnel inlet/outlet at the front end of the microfluidic hybridization chip 20 and the thin pipe 612 is sealed. Such a connection for different tunnels is simple, convenient, and cheap.

Figure 6:
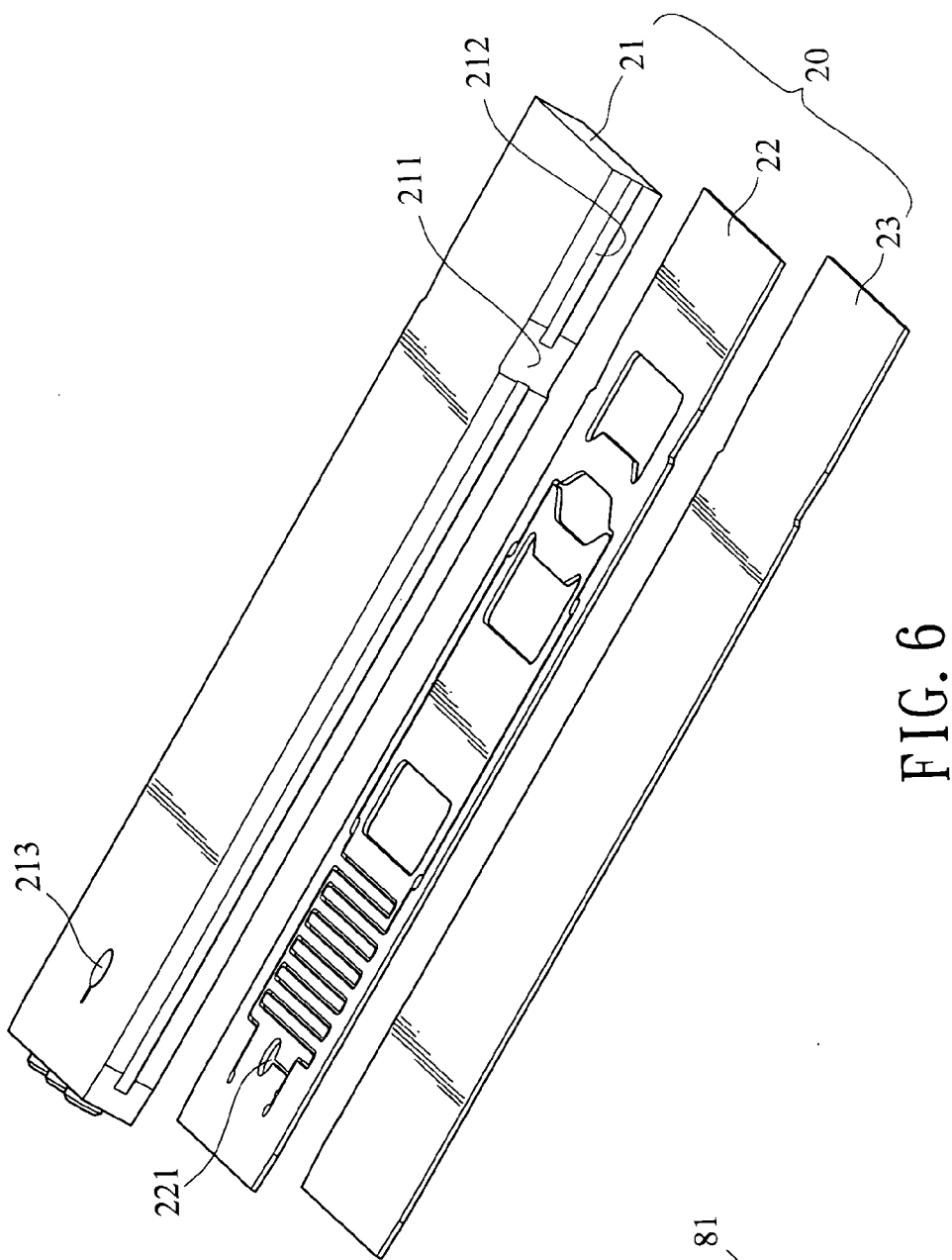
FIG. 6 is an exploded diagram of the microfluidic hybridization chip.
Figure 8:
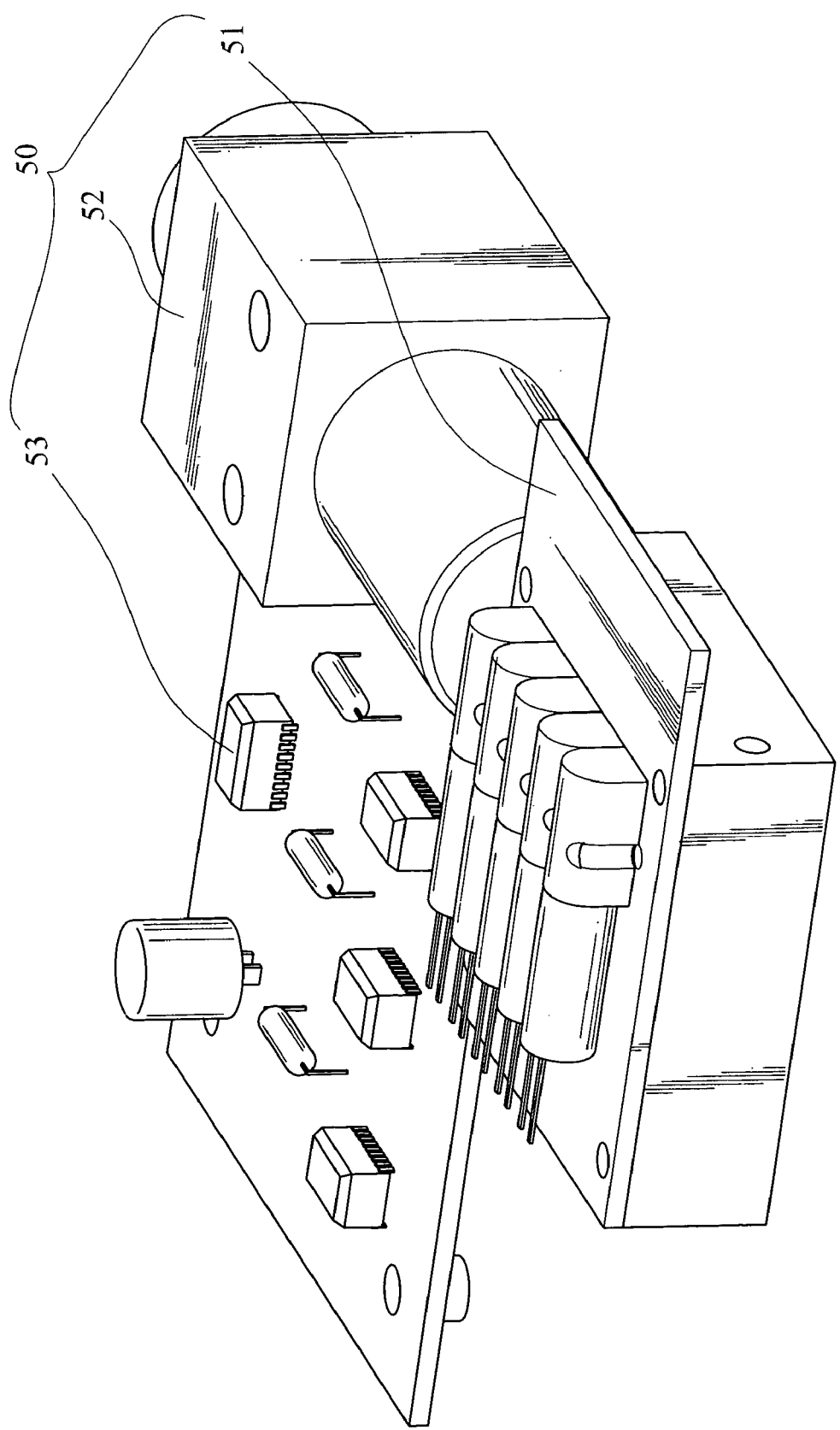
FIG. 8 is a schematic view of the flow control system.

With reference to FIG. 6, the microfluidic hybridization chip 20 is designed to have a multiple-layer structure, mainly containing an upper cover 21, a tunnel layer 22, and a lower cover 23. The material of the microfluidic hybridization chip 20 can be selected from polymers (PMMA, PET, PDMS, PVC, PS, PC, and so on) and glasses. The upper cover 21 is formed with the positioning holes 211, the sliding tracks 212, and the sample inlet/outlet 213. It along with the lower cover 23 sandwiches the tunnel layer 22. The tunnel layer 22 can be designed to have a multiple-layer structure too for providing microfluidic tunnels and reactions. The tunnel layer 22 includes a sample receiving region 221, a mixing and denature region 222, a hybridization and testing region 223, a waste solution region 224, and heat insulating regions 225, 226, 227 (see FIG. 8). Such a multiple-layer design of microfluidic hybridization chip 20 can have several layers to satisfy various kinds of needs. The manufacturing method is to make each layer separately and then to combine them using bonding techniques (such as thermal bonding). The multiple-layer structure can be formed by injection molding to directly form the micro tunnel on the lower cover.

Figure 9:
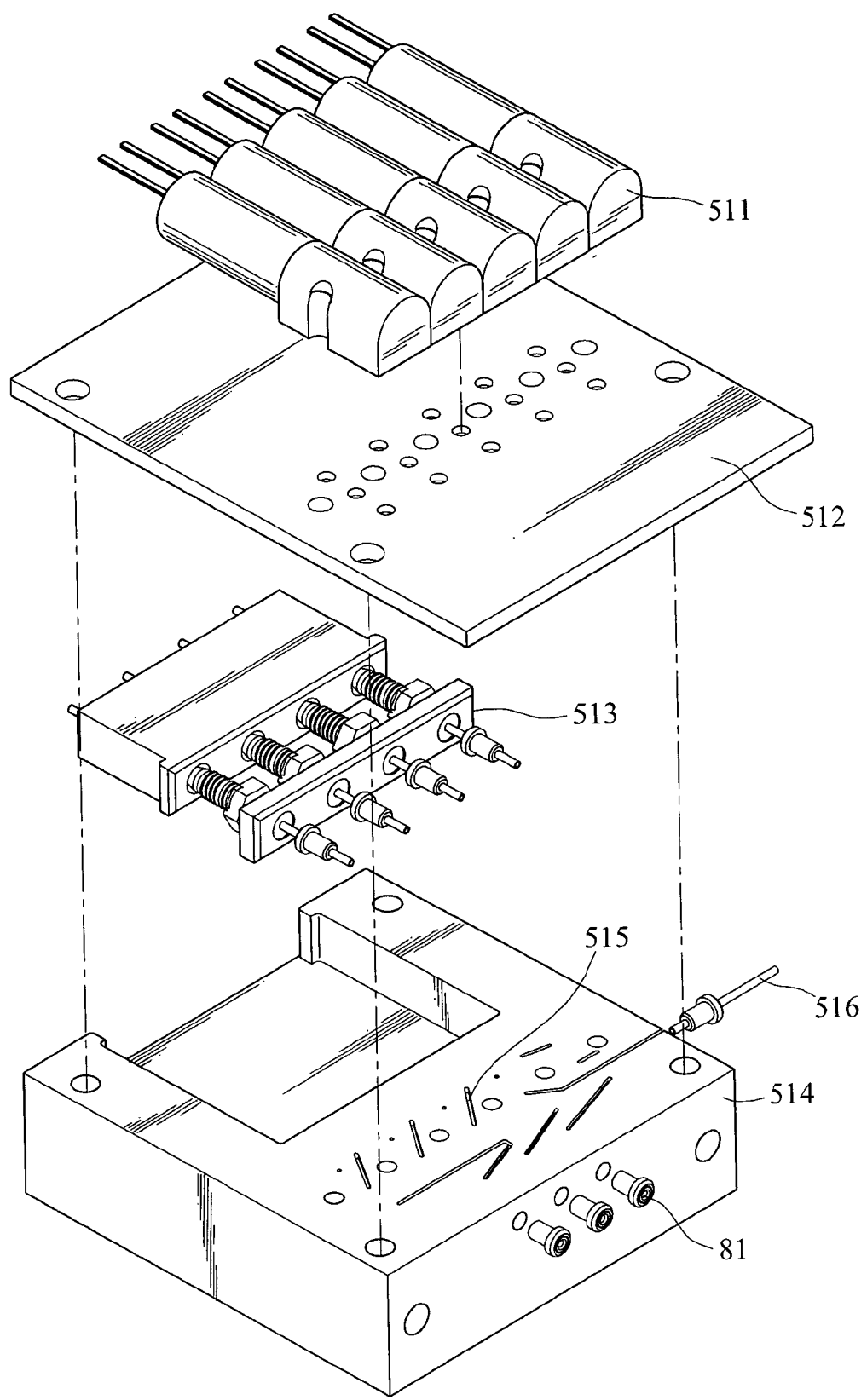
FIG. 9 is a schematic view of the flow transmission module.
Figure 10:
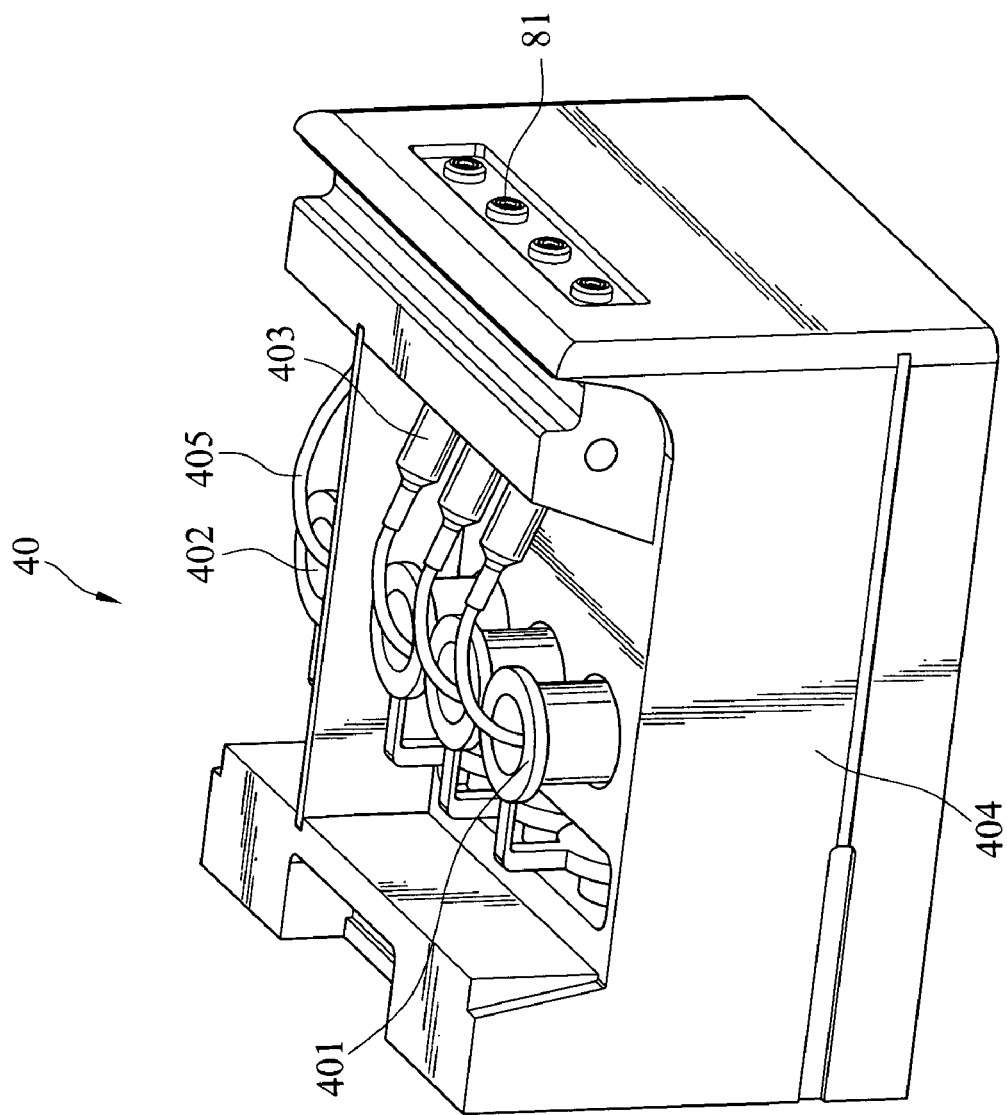
FIG. 10 is a schematic view of the test agent support.

The flow control system 50 of the microfluidic hybridization chip contains a control circuit 53, a driving pump 52, and a micro flow transmission module 51. The control circuit 53 controls the driving pump 52 and the micro flow transmission module 51 for controlling the fluid in and out of the microfluidic hybridization chip 20. The driving pump 52 is mainly used as the power source of transporting the fluid. It can be an injection pump, pneumatic pump, a thermol actuated pump, and a piezoelectric pump and so on. The main functions of the flow transmission module 51 are to send the test agent inside the test agent support 40 into the microfluidic hybridization chip 20 and to send the reacted waste solution to a waste pipe. The reaction test agent flow required during the hybridization is totally controlled by the flow transmission module 51. Its main structure is shown in FIG. 9. It includes a flow switch valve 511, a flow transmission module upper cover 512, a thin pipe module 513, and a flow transmission lower cover 514. The upper cover 512 and the lower cover 514 are fixed using screws (not shown). The front end of the lower cover 514 is installed with three elastic sleeve rings 81 for sealing the thin pipes 612 of the microfluidic hybridization chip support 60 and the flow transmission module 51. The sealing principle and means are similar to those mentioned before. The connection between the driving pump 52 and the flow transmission module 51 is also secured using thin pipes 516 with plastic sleeve rings. Moreover, the connection between the flow transmission module 51 and the test agent support 40 is achieved in the same way, installing a thin pipe on a fixing block to form a thin pipe module 513. Therefore, the driving pump 52 controls the in and out of the fluid via the flow switch valve 511. In this manner, the test agent support 40 and the flow transmission module 51 are connected to the microfluidic hybridization chip 20 via the micro tunnel 515.

The test agent support 40 contains a base 404, which is connected to a soft tube 405 using a connection pipe 403. It also supports several test agent bottles 401 and a waste solution bottle 402. When the support is inserted into the platform base 30, its fixing method is using positioning pins along with the positioning holes and sliding tracks on the base as described above. The test agent support 40 also includes a support upper cover to prevent dusts from entering the test agent storage area (FIG. 2).

After the test sample is dropped into the sample receiving region 221 through the sample inlet/outlet 213, a tape is used to seal the sample inlet/outlet 213. The microfluidic hybridization chip 20 is then inserted into the microfluidic hybridization chip support 60. At the moment, the driving pump 52 starts to drag the sample into the mixing and denature region 222. Due to the long and meander design of the mixing and denature region 222, the sample and the test agent can be fully mixed. Once the denature is completed, the sample solution is directed to the hybridization and test region 223. When the sample solution reaches the hybridization and test region 223, the driving pump 52 keeps performing the pumping and pushing actions to facilitate the hybridization reactions. At this moment, one can control to have some mixed solution flow into the mixing and denature region 222, allowing yet hybridized double-helix DNA's to denature. Finally, the denature DNA are sent back to the hybridization and test region 223 for further hybridization. Such processes are continued for several times until full hybridization is achieved. To facilitate the hybridization efficiency, the hybridization and test region 223 is installed with a micro vibrator (not shown) to enhance the reaction rate. The heating plate concaves 624, 625 are also installed with heaters to heat up the hybridization and test region 223 and the mixing and denature region 222. They can be controlled by a contact pad 623 that is in electrical communications with the microfluidic hybridization chip 20. To ensure that heat is not released to other areas, heat-insulating areas 225, 226, 227 are designed on both sides to avoid heat from leaking. The heat-insulating areas 225, 226, 227 can be formed by forming several vacant regions in the tunnel layer 22 or filling heat-insulating materials therein.

Figure 11:
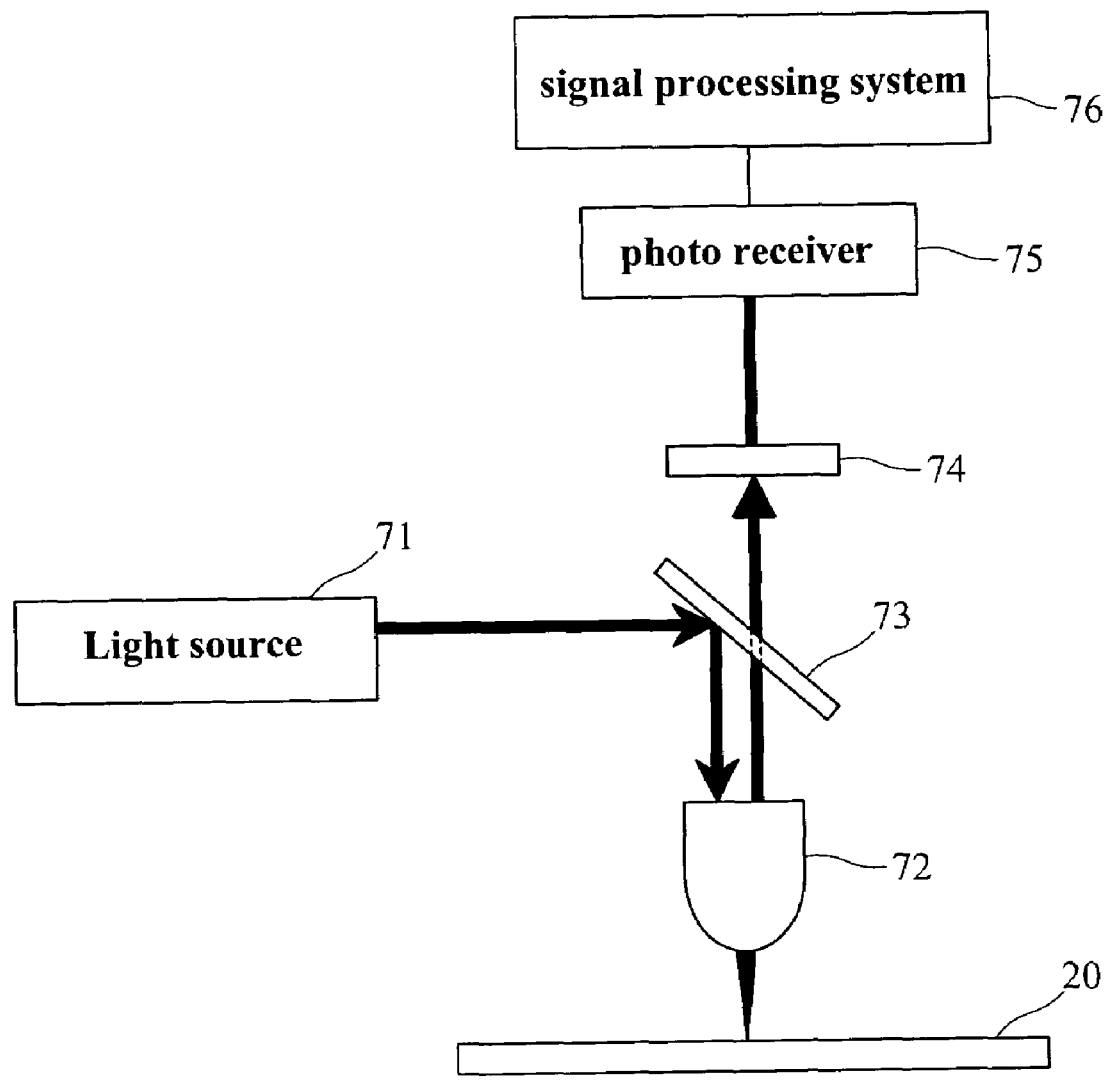
FIG. 11 is a schematic view of the signal detection system.

After the reaction is completed, a signal detection system is used for tests. Such a system can be a fluorescence detection system. As shown in FIG. 11, a light source 71 along with a beam splitter 73 and an object lens 72 excites fluorescent dye molecules on a probe to radiate a fluorescent signal. The fluorescent signal passes through a filter 74 to get rid of unnecessary noise light. The filter light is received by a photo receiver 75, which then sends it to a signal processing system 76. The light source 71 can be a LED, laser or a mercury light bulb. It is mainly used to excite the fluorescent dye molecules on the probe. The photo receiver 75 can be a charge coupled device (CCD) or a photo multiplier tube (PMT). The disclosed signal detection system can be directly installed the platform to perform direct tests on the microfluidic hybridization chip 20. After the detection, the waste solution can be sent to the waste bottle 402 using the same control system.

In comparison with the prior art, the invention provides a hybridization detection system with a faster reaction rate, automatic operations, and a lighter weight:
1. The invention has a small platform design. The disclosed auto control system includes the test agent transmissions, positioning controls, hybridization monitoring, and detection signal controls. All of them can be controlled through a touch-control monitor. It is very convenient and simple.
2. The invention is based upon the idea of a microfluidic chip and aims at providing rapid and correct results.
3. The disclosed microfluidic chip hybridization platform can accommodate chips of different purposes.

Certain variations would be apparent to those skilled in the art, which variations are considered within the spirit and scope of the claimed invention.

What is claimed is:
1. An auto microfluidic hybridization chip platform for performing nucleic acid hybridization on a sample, comprising:
 a test agent support which holds at least one test agent bottle of a test agent and has a connection pipe connecting the test agent support to the test agent bottle;
 a microfluidic hybridization chip, comprised of:
  a sample receiving region which receives the sample in use;
  a mixing and denaturing region which is connected to the sample receiving region to receive the test agent, driven by an external force to mix the test agent and the sample and, through a meandering path, fully mixes the sample and the test agent for denaturing; and
  a hybridization and test region which connects to the mixing and denaturing region for the mixture of the sample and the test agent to perform hybridization reactions;
 wherein the microfluidic hybridization chip has at least one micro tunnel embedded inside the microfluidic hybridization chip, which connects the sample receiving region, the mixing and denaturing region, and the hybridization and the test region, for providing the sample and/or the test agent pass through the regions;
 a microfluidic hybridization chip support having an accommodation space with corresponding upper covers on both sides thereof for the insertion of the microfluidic hybridization chip therein; and
 a flow control system, connected to the test agent support via a connection pipe, the flow control system comprising:
  a micro flow transmission module, connected to the test agent bottle and to the microfluidic hybridization chip support, the micro flow transmission module for transporting fluid and controlling fluid flow so that, in use, the microfluidic hybridization chip is in fluid flow communication with the test agent bottle or test agent support via the microfluidic hybridization chip support and the micro flow transmission module; and
  a driving pump, connected to the micro flow transmission module, the driving pump for driving the fluid to flow through the micro flow transmission module and the at least one micro tunnel.

2. The auto microfluidic hybridization chip platform of claim 1, further comprising a platform base for supporting the test agent support, the flow control system, and the microfluidic hybridization chip.

3. The auto microfluidic hybridization chip platform of claim 1, wherein the connection pipe of the test agent support is installed with an elastic sleeve ring to ensure a seal in use.

4. The auto microfluidic hybridization chip platform of claim 1, wherein the microfluidic hybridization chip has a front end which is slanted and which corresponds to the accommodation space of the microfluidic hybridization chip support for the insertion of the microfluidic hybridization chip therein.

5. The auto microfluidic hybridization chip platform of claim 1, wherein the microfluidic hybridization chip support has a groove defined therein and a positioning pin, and wherein the microfluidic hybridization chip has a positioning point for fixing the position of the microfluidic hybridization chip within the groove of the microfluidic hybridization chip in use.

6. The auto microfluidic hybridization chip platform of claim 1, wherein the microfluidic hybridization chip further comprises an upper cover, a tunnel layer, and a lower cover, and wherein the tunnel layer is sandwiched between the upper cover and the lower cover to form the sample receiving region, the mixing and denaturing region, and the hybridization and test region.

7. The auto microfluidic hybridization chip platform of claim 6, wherein the tunnel layer consists of a plurality of tunnel plates.

8. The auto microfluidic hybridization chip platform of claim 1, wherein the flow control system includes the driving pump is the power source of the fluid transmissions.

9. The auto microfluidic hybridization chip platform of claim 8, wherein the driving pump is selected from the group consisting of an injection pump, a pneumatic pump, a thermally actuated pump, and a piezoelectric pump.

10. The auto microfluidic hybridization chip platform of claim 1, wherein the microfluidic hybridization chip has a bottom region which contains a heater at each of the positions corresponding to the mixing and denaturing region and the hybridization and test region, respectively, to increase the reaction rate in use.

11. The auto microfluidic hybridization chip platform of claim 10, wherein a heat-insulating region is provided between the mixing and denaturing region and the hybridization and test region for block heat exchanges between both sides in use.

12. The auto microfluidic hybridization chip platform of claim 11, wherein the heat-insulating region is formed by a means selected from the group consisting of excavating the microfluidic hybridization chip and filling the microfluidic hybridization chip with heat-insulating materials.

13. The auto microfluidic hybridization chip platform of claim 1, wherein the microfluidic hybridization chip further comprises a waste solution region connecting to the hybridization and test region and to the flow control system for the reacted waste solution to be dumped by the flow control system into an empty test agent bottle on the test agent support in use.

14. The auto microfluidic hybridization chip platform of claim 13, wherein the waste solution region is installed with an elastic sleeve ring to ensure a seal in use.

15. The auto microfluidic hybridization chip platform of claim 1, further comprising a signal detection system provided next to the microfluidic hybridization chip for detecting the hybridization result of the mixed solution in use.

16. The auto microfluidic hybridization chip platform of claim 15, wherein the signal detection system is a fluorescence detection system that uses a light source to excite fluorescent dye molecules on a probe, which radiate a fluorescent signal that is filtered and received by a photo receiver.

17. The auto microfluidic hybridization chip platform of claim 16, wherein the light source is selected from the group consisting of a LED, a laser and a mercury light bulb.

18. The auto microfluidic hybridization chip platform of claim 16, wherein the photo receiver is selected from the group consisting of a charge coupled device (CCD) and a photo multiplier tube (PMT).

19. The auto microfluidic hybridization chip platform of claim 1, further comprising a case that has a window exposing the microfluidic hybridization chip.

20. The auto microfluidic hybridization chip platform of claim 1, wherein the micro flow transmission module comprises a flow switch valve, a thin pipe module and a cover.

* * * * *